United States Patent [19]
McKellin et al.

[11] 4,328,360

[45] May 4, 1982

[54] POLYPEROXY COMPOUNDS

[75] Inventors: Wilbur H. McKellin, Buffalo; James R. Kolczynski, Williamsville; Orville L. Mageli, Kenmore; Antonio J. D'Angelo, Buffalo, all of N.Y.

[73] Assignee: Pennwalt Corporation, Philadelphia, Pa.

[21] Appl. No.: 118,380

[22] Filed: Feb. 5, 1980

Related U.S. Application Data

[62] Division of Ser. No. 285,857, Jun. 6, 1963.

[51] Int. Cl.$^3$ .......................... C08F 8/06; C07C 69/00
[52] U.S. Cl. .................................... 560/129; 525/332; 525/386
[58] Field of Search ................. 260/453 RZ; 560/129

[56] References Cited

U.S. PATENT DOCUMENTS 3,433,825  3/1969  Maltha et al. .................. 260/478

FOREIGN PATENT DOCUMENTS 985737  3/1965  United Kingdom ............... 260/478

*Primary Examiner*—William F. Hamrock

[57] ABSTRACT

A polyperoxyketal compound is provided having at least one carboxy group, a hydrocarbon ester. An example of this compound is n-butyl gamma,gamma-bis(t-butylperoxy)valerate. This polyperoxyketal compound is used as a vulcanizing agent for thermoplastic polymers such as rubber and ethylene-propylene rubber.

6 Claims, No Drawings

POLYPEROXY COMPOUNDS

This is a division of application Ser. No. 285,857, filed June 6, 1963.

This invention relates to new polyperoxy compounds; to vulcanizible compositions of these compounds and certain polymers; to the vulcanized compositions; and to methods of cross-linking certain polymers.

Ethylene-propylene rubber, an elastomeric copolymer or terpolymer, is now on the market. It is very desirable for many purposes because of its resistance to weathering and ozone. It can be vulcanized (cross-linked) to a thermoset material with a cross-linking agent (vulcanizing agent). The present cross-linking agents are expensive or, make a product having a bad odor. Others require too high a temperature for reasonable curing times.

EPR is subject to scorching with some agents. Other agents react so slowly at the temperatures available on conventional equipment, 300°–325° F., that the heat cure time is too long; suitable times require temperatures which cannot be used because of equipment limitations.

Certain polyperoxy compounds are now used as cross-linking agents for EPR—these have one or more of the drawbacks listed above.

EPR is only one of the natural and synthetic polymers whose ultimate use, or possible uses, are determined by the characteristics of a cross-linked product. The presently known polyperoxy compounds leave something to be desired when used as cross-linking agents for polymers which can be cross-linked to form thermoset materials.

An object of the invention is a polyperoxy compound of particular utility in the cross-linking of polymers. A special object is a polyperoxy compound of utility in cross-linking (vulcanizing) ethylene-propylene rubber. Other objects are cross-linked polymeric materials and methods to produce these. Still other objects will become apparent during the reading of the detailed description of the invention.

THE POLYPEROXY COMPOUNDS

We have discovered a new class of polyperoxy compounds which have at least two peroxy groups (—OO—). One oxygen atom of each of two of these peroxy groups is linked to a common carbon atom; the other oxygen atom of each of these peroxy groups is linked to a tertiary carbon or silicon atom of an organo group; preferably a hydrocarbon or silyl group. (These two defined peroxy groups are hereinafter spoken of as "a pair".) A simplified configuration of one pair may be set out as:

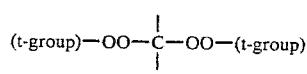

The common carbon atom is part of an aliphatic group which has at least two carbon atoms and includes at least one carboxy group. The carboxy group(s) includes the acid (—COOH), and/or the acid anhydride

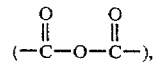

and/or the ester (—COOR), and/or the metal salt (—COOM).

More specifically these new polyperoxy compounds include compounds which are, for convenience, desirable as reaction products, i.e., derivable from the reaction, of t-organo hydroperoxide with one or more of these acid reactants: (a) carbonyl aliphatic hydrocarbon carboxylic acids, (b) carbonyl aliphatic hydrocarbon carboxy esters, and (c) carbonyl aliphatic hydrocarbon carboxylic acid anhydrides and; (d) the metal salts where the acid member has 2–36 carbon atoms; and the ester group is derivable from aliphatic hydrocarbon alcohols, aliphatic hydrocarbon ether alcohols, cycloaliphatic hydrocarbon alcohols, aromatic hydrocarbon alcohols and oxyheterocyclic alcohols.

It is preferred that the new compounds have 4–7 carbon atoms in said aliphatic group and only saturated linkages between carbon atoms, and in the case of the ester compounds, the ester group is straight chain aliphatic hydrocarbon having 1–18 carbon atoms. Also that there be present (a) not more than two pairs of peroxy groups; (b) only one of said carboxy groups; and (c) the aliphatic group having the common carbon atom(s) be straight chain.

For purposes of illustration only, simplified structural configurations of individual compounds of the invention are set forth below.

I. Product of t-butyl hydroperoxide and levulinic acid; gamma, gamma-bis(t-butylperoxy) valeric acid; 4,4-bis(t-butylperoxy) pentanoic acid.

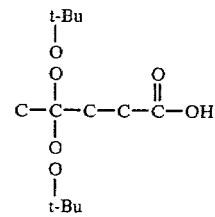

II. n-butyl ester of I; n-butyl gamma, gamma-bis(t-butylperoxy) valerate; n-butyl 4,4-bis(butylperoxy) pentanoate.

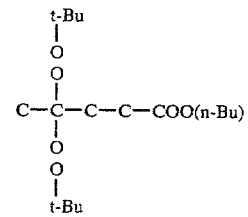

III. Acid anhydride of I; gamma, gamma-bis(t-butylperoxy) valeric acid anhydride; 4,4-bis(t-butylperoxy) pentanoic acid anhydride.

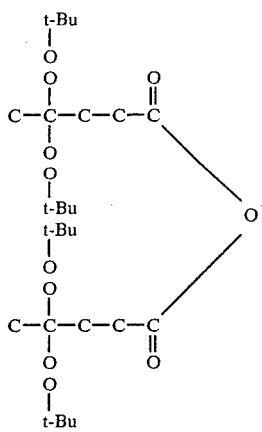

THE HYDROPEROXIDES

The compounds of the invention may be described as reaction products of certain hydroperoxides and of certain carbonyl aliphatic carboxy compounds. The hydroperoxide may be set forth as: (t-organo)—O—O'—H where O and O' are oxygen and "O" is linked to a tertiary carbon atom or silicon atom of an organo group. More commonly the tertiary atom is part of an aliphatic, cycloaliphatic, aromatic and organo-silicon groups. Usually the tertiary atom is part of an aliphatic hydrocarbon, cycloaliphatic hydrocarbon, aralkyl hydrocarbon or silyl group having not more than about 24 carbon atoms or silicon atoms and/or carbon and silicon atoms. Illustrative hydroperoxides are: t-butyl hydroperoxide, cumyl hydroperoxide, t-amyl hydroperoxide, penanyl hydroperoxide, p-menthane hydroperoxide, 2-methyl-2-hydroperoxy-pentanol-4, and trimethyl silyl hydroperoxide.

THE CARBONYL ACIDS

The carbonyl reactant may be any carbonyl aliphatic carboxylic acid having at least two carbon atoms. The carbonyl group may be aldehydo and/or keto. More than one aldehydo group or keto group may be present. The acid may have more than one carboxy group. The keto group(s) may be positioned on any internal carbon atom in the aliphatic group. The carboxy group(s) may be located on any position in the aliphatic group. The aliphatic group may be saturated, i.e., have only single bonds between carbon atoms, or it may be unsaturated having ethylenic or acetylenic bonds.

Although the size of the molecule as determined by acid reactant is not material to the ability to prepare the novel compounds, the acids commonly used have 2-36 carbon atoms and are carbonyl aliphatic hydrocarbon carboxylic acids.

The keto-acids are preferred; desirably those having 3-18 carbon atoms and especially those with 4-7 carbon atoms, and in particular these in a straight chain saturated aliphatic hydrocarbon group. In general, it is preferred to use keto-acids having 1 or 2 keto groups; only one carboxyl group, and a straight chain configuration.

More commonly the acid reactant is a monoketo aliphatic hydrocarbon monocarboxylic acid having 2-36 carbon atoms; more usually 3-18 carbon atoms; and more desirably is saturated.

Illustrative acids are: glyoxalic acid, pyruvic acid, levulinic acid, 12-ketostearic acid, acetoacetic acid and chlorolevulinic acid.

THE CARBONYL ACID ANHYDRIDES

The carbonyl reactant may be any acid anhydride of the same or different carbonyl aliphatic carboxylic acids, each having at least two carbon atoms; or of a carbonyl aliphatic carboxylic acid, having at least two carbon atoms, with an aliphatic carboxylic acid having no carbonyl group. (When one acid has no carbonyl group present, it is considered herein to be in effect an ester group and the statements made hereinafter with respect to the ester group in carbonyl acid ester reactants apply.)

It is preferred to use the acid anhydrides of two carbonyl aliphatic carboxylic acids, each having at least two carbon atoms. The description of the carbonyl aliphatic carboxylic acid reactant set out in the preceding section is applicable to each acid member of the carbonyl acid anhydride reactant; in other words the acid anhydride is regarded herein as a number of linked acid members with the carbon atom content, the carbonyl group content and other substituent content totaling the sum of each member—less the $H_2O$ lost in the dehydration to the acid anhydride state.

The acid anhydride may include one or more free carboxyl group(s), or one or more ester groups, when the acid member(s) includes more than one carboxyl groups, e.g., the acid anhydride of ketoheptanedioic acid and levulinic acid. More than one anhydride group may be present.

Illustrative acid anhydride reactants are: levulinic acid anhydride; ketoheptanedioic acid monoanhydride; levulinic acid anhydride with pyruvic acid; 12-ketostearic acid anhydride; acetoacetic acid anhydride and chlorolevulinic acid anhydride.

THE CARBONYL ACID ESTERS

The carbonyl aliphatic carboxy reactant may include one or more ester groups. The description of the carbonyl aliphatic carboxylic acids in the foregoing section applies completely to the "acid portion" of the ester reactant; also the description of the carbonyl aliphatic carboxylic acid anhydrides in the above section applies when an ester group is present. It is to be understood that herein "ester group" is intended to apply to "R" in the (—COOR) group present in the reactant and also in the final polyperoxy compound.

The ester group may be aliphatic, cycloaliphatic, aromatic or heterocyclic. Preferably the ester group does not include a carbonyl group. Typically the ester group may include one or more hydroxy (—OH) groups; halogen (halo) atoms; and ether (oxy) linkages.

Although the ester group may be derived from any aromatic alcohol, it is preferred to use the aromatic hydrocarbon and particularly benzenoid alcohols, such as benzyl alcohol. The heterocyclic group may include any atom, such as oxygen, nitrogen or sulfur, but it is preferred to use, as the ester group source, oxyheterocyclic alcohols.

It is preferred to use as the ester group source cycloaliphatic hydrocarbons having 6-30 carbon atoms; cyclohexanol is a particularly preferred cyclic alcohol.

Commonly the ester group is derived from aliphatic hydrocarbon alcohols or aliphatic hydrocarbon ether alcohols, such as methyl alcohol, n-butyl alcohol, stearyl alcohol, triacontyl alcohol, ethylene glycol, 1,6-hexanediol, diethylene glycol, tetrapropylene glycol, glycerol, pentaerythritol, trimethylolpropane, butenediol, propargyl alcohol and butynediol. The preferred alcohols may be described as aliphatic alcohols having 1–30 carbon atoms and only carbon, hydrogen and oxygen atoms and no carbonyl groups. The straight chain aliphatic hydrocarbon alcohols having 1–18 carbon atoms are particularly preferred.

Illustrations of polyperoxy-ester affording compounds are: n-butyllevulinate; diethyl 4-ketoheptane-1,7-dioate; ethyl ketopropionate; ethyl ketobutyrate; allyl levulinate; isopropyl levulinate; n-butyl ketoheptanoate; n-butyl ketohexanoate; 2-ethylhexyl levulinate; n-dodecyl levulinate; methyl levulinate; ethylene bis-levulinate (the diester of ethylene glycol and levulinic acid) where ethylene represents the ($-CH_2-CH_2-$) group, ethyl acetoacetate, and the polycondensate of ketoazelaic acid with ethylene glycol.

PREPARTION OF ILLUSTRATIVE POLYPEROXY COMPOUNDS

The polyperoxy compounds of the invention can be made by one or more of the procedures known to this art. Suitable procedures are taught in U.S. Pat. No. 2,455,569, granted Dec. 7, 1948 and in U.S. Pat. No. 2,537,853, granted Jan. 9, 1951.

For purposes of illustration only, the preparation is set out of three species using t-butyl hydroperoxide and levulinic acid or a derivative thereof.

IV. gamma, gamma bis(t-butylperoxy) valeric acid

A mixture of 23.3 g. of levulinic acid and 38.4 g. of 93.75% t-butyl hydroperoxide was stirred at 32°–41° F. while 19.2 g. of 77% sulfuric acid solution was slowly added.

After a reaction time of four hours, the sulfuric acid layer was separated and the organic layer washed with saturated sodium chloride solution. Remaining unreacted t-butyl hydroperoxide was removed under reduced pressure at 86° F.

The product gamma, gamma bis(t-butylperoxy) valeric acid, was found to be 90% pure as determined by assay for active oxygen.

V. n-butyl, gamma, gamma bis(t-butylperoxy) valerate

In a representative procedure 757 g (7.7 moles) of t-butyl hydroperoxide-90 was added to 603 g (3.5 moles) of n-butyl levulinate and the mixture cooled to 23°–32° F., 378 g of 77% sulfuric acid was added slowly while the temperature was held below 32° F. The total addition time was 30 minutes. The reaction mixture was stirred at 28°–32° F. for 1½ hours after the addition was complete. The acid layer was allowed to settle and was drained from the reactor. Saturated sodium chloride solution (250 ml) was added to the reactor and the pH adjusted to about 8 by the addition of 10% sodium hydroxide solution and 5% sodium bicarbonate solution. After warming to 68° F. the aqueous layer was separated and the wet product submitted for analysis. A yield of 1208 g of product assaying 81% n-butyl gamma, gamma bis(t-butylperoxy) valerate and corresponding to an 82.2% yield of product was obtained.

VI. gamma, gamma bis(t-butylperoxy) valeric acid anhydride

It has been discovered that the polyperoxy acids of this invention are surprisingly stable and can be dehydrated to the polyperoxy acid anhydride without affecting the peroxy group.

To a mixture of 83.4 g. (0.3 mole) of gamma, gamma bis(t-butylperoxy) valeric acid, 400 ml of benzene and 47.4 g. (0.6 moles) of pyridine at room temperature there was added, dropwise, 30 g. (0.39 moles) of acetyl chloride over a period of 5 minutes. The temperature rose to about 100° F. as the addition progressed. Stirring was continued for 30 minutes at this temperature of about 100° F. Stirring was continued for an additional 30 minutes at a temperature of about 104°–113° F.

After this time the reaction mixture was cooled to about 50° F. and the solid pyridine hydrochloride by-product was filtered off. The organic phase was stripped under reduced pressure to eliminate the benzene, the excess pyridine, and the acetic acid by-product.

A viscous liquid was obtained in good yield that on standing solidified—M.P., 95°–97° F. The active oxygen content found was 11.75%. The theoretical active oxygen for the acid anhydride is 11.89%.

VII. gamma, gamma bis(t-butylperoxy) valeric acid

The known peroxy compounds are not stable in presence of acids or bases at relatively high temperatures (140°–212° F.). Now, it has been discovered that it is possible to treat n-butyl gamma, gamma bis(t-butylperoxy) valerate with base at 140°–212° F. and obtain in good yield gamma, gamma bis(t-butylperoxy) valeric acid.

Into a 5 liter three-necked round bottomed flask, equipped with stirrer, thermometer and reflux condenser was placed 725 g. (2 moles) of n-butyl gamma, gamma bis(t-butylperoxy) valerate (92%) and 800 g. (4 moles) of NaOH (20%). The mixture was heated gradually at 156°–160° F. for two hours. At the end of this period the saponification was complete. The butyl alcohol and the water present were distilled off under reduced pressure until a solid mass was obtained. The solid was dissolved in three liter of water and the gamma, gamma bis(t-butylperoxy) valeric acid was precipitated with one liter of 6 N HCl solution.

The white crystals were filtered off and washed with water to neutral and then air dried. A yield of 400 g was obtained. The solid had an M.P. of 176°–178° F.; an active oxygen content of 11.59%. The active oxygen content calculated for $C_{13}H_{26}O_6$ is 11.51%.

METAL SALTS

It has been discovered that the metal salts of the aforesaid polyperoxycarboxylic acids can be prepared without disrupting the polyperoxy groups. These metal salts are significantly effective as cross-linking agents. Any metal may be present. However the alkali metals, the alkaline earth metals and the heavy metals are preferred. Illustrative of the salts which can be prepared are barium; calcium; lithium; and zinc salts of gamma, gamma bis(t-butylperoxy) valeric acid. The ammonium and the amine salts are also new compounds. Amides, such as 4,4-bis(t-butylperoxy) pentonamide, are also new.

UTILITY

The above described polyperoxy aliphatic carboxy compounds are suitable for any purpose wherein the peroxy group is useful. These compounds are effective cross-linking agents for polymers and especially effective for elastomers such as ethylene-propylene rubber.

The compounds of the invention are characterized by good efficiency, i.e., the number of cross-linkages obtained from the peroxy groups present, as compared to the bis(t-butylperoxy) alkanes.

It has been found that the polyperoxy compounds can be positioned on a carrier (support) when the ultimate use makes such a composition desirable, as for example, in rubber compounding. Any solid which does not react with the polyperoxy compound may be used as a carrier. Suitable are silicates, clays, talc, magnesium carbonate and carbon blacks. Especially preferred are the silicates and magnesium carbonate. A blend of n-butyl gamma, gamma bis(t-butylperoxy) valerate and a synthetic silicate has been found very suitable in rubber compounding.

COMPOSITIONS AND METHOD

It has been discovered the defined polyperoxy compounds of the invention are effective cross-linking (vulcanizing) agents for polymeric compounds which are capable of being cross-linked to form a thermoset material. The defined polyperoxy compound is present in intimate admixture with the polymeric compound in an amount sufficient to afford the desired degree of cross-linking. (Herein the word of art "vulcanizing" and "cross-linking" are used as synonyms.)

THE POLYMERIC COMPOUNDS

The polymeric compounds include any of those natural and synthetic materials which are thermoplastic or have indefinite melting points and which can be transformed to thermoset materials—elastic, or more or less, rigid solids—by a cross-linking reaction, especially through the action of an added agent. For example, the vulcanizing of natural and synthetic rubber by means of sulfur or peroxy compounds.

Illustrative classes and sub-class of polymeric compounds are: The solid polyolefins such as polyethylene, especially the low density polymer; polypropylene; and polybutenes—viscoresins. The elastomers such as natural rubber; the synthetic rubbers including butyl rubber, Gr-S rubber, neoprene, acrylic rubber, Buna rubber, ethylene-propylene rubber and the silicone rubbers. The vinyl polymers such as polyvinyl chloride, polyvinyl acetate, PVC-PVAC copolymers, ethylene-vinyl chloride copolymer, and the vinyl pyrollidone polymers and copolymers. Miscellaneous "elastomers" such as polybutene-styrene copolymers; ethylene and/or propylene-styrene copolymers; ABS copolymers. Also the various polyether resins, polyester resins, polyamide resins and the natural gums. The solid polyolefins and elastomers are especially suitable polymeric compounds. The polymers may include plasticizers and/or oil extenders.

VULCANIZIBLE COMPOSITIONS

It has been discovered that an intimate mixture of the defined polymer and the defined polyperoxy compound agent can be heat-cured in reasonable times at reasonable temperatures to a cross-linked (vulcanized) material. The temperature and time are controlled to obtain the desired degree of cross-linking. Sufficient agent is present to afford the desired degree of cross-linking.

The polyperoxy compounds of the invention can be used alone or in conjunction with a coagent or coupling agent—just as the presently known vulcanizing agents are used. Suitable coagents are sulfur; viscous polybutadiene resin such as Enjay Buton 150; ethylene dimethacrylate; maleic acid; vinyl silane; N,4-dinitroso-N-methyl aniline; and hexachloropentadiene.

In the vulcanization of solid polyolefins and elastomers the polyperoxy compound desirably is one that is derivable from the reaction of the defined hydroperoxide and a keto aliphatic hydrocarbon carboxylic acid, ester, metal salt or acid anhydride having 3–18 carbon atoms in the acid portion and the ester portion, if any, is derived from an aliphatic alcohol having 1–30 carbon atoms and having only carbon, hydrogen and oxygen atoms and no carbonyl groups.

Especially good results are obtained with elastomers and solid polyolefins when the polyperoxy compound has 4–7 carbon atoms in a saturated aliphatic hydrocarbon group and includes at least one —COOH; —COOR; —COOM or

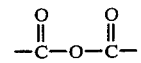

group, where R is a straight chain aliphatic hydrocarbon group having 1–18 carbon atoms and where M is a metal ion. Preferably the polyperoxy compound has not more than two pairs of the polyperoxy groups, only one acid group and the aliphatic group is straight chain.

In addition to the defined polymeric compound and defined polyperoxy compound, in intimate mixture, the vulcanizible composition may include coagents, promoters, coupling agents, fillers, reinforcing materials, and any other material conventionally used in the production of vulcanized compositions. Desirable fillers are carbon black, titanium dioxide, calcium silicate and the alkaline earth metal carbonates.

A typical mix includes, as parts by weight per 100 parts by weight of polymeric compound: EPR (an ethylenepropylene copolymer), 100; the aforesaid preferred polyperoxy compound, 1–5; a coagent, such as sulfur 0.1–0.5; carbon black, 50–60. Other coagents usually require different amounts.

EPR vulcanizates are excellent for articles such as garden hose. A typical formulation for the cover is: EPR, 100; clay (hard), 50; silicate, 20; talc, 50; oil, 10; zinc oxide, 5; vinyl silane, 5; viscous polybutadiene, 5; and n-butyl gamma, gamma bis(t-butylperoxy) valerate-carrier, 5.0. For the tube: EPR, 100; carbon blacks, 175; oil, 10; viscous polybutadiene, 10; and n-butyl gamma, gamma bis(t-butylperoxy) valerate-carrier, 4.0; the valerate-carrier blend was about equal parts by weight of the valerate and finely divided filler.

A suitable EPR for these formulations contains about 43 weight percent of ethylene and about 57 weight percent of propylene in the polymer; has a specific gravity of about 0.86; a Mooney viscosity, 8 m L/212° F.(100° C.) of 40; and an ash content of about 0.2 weight percent.

Oil extended EPR is used in formulations. A typical extrusion formulation using such an EPR is: extended EPR, 100 rubber—40 oil; carbon black, 180; hydrocarbon oil, 30; sulfur, 0.3; and n-butyl gamma, gamma bis(t-butylperoxy) valerate, 3.5.

This extended EPR is a blend of 100 parts by weight of the above EPR and 40 parts by weight of mineral oil; this blend has a specific gravity of 0.86: a Mooney viscosity, 8 m L/212° F. of 40; and an ash content of 0.6 weight percent.

The vulcanizible composition requires that the solid polymeric compound and the cross-linking agent and the other materials in the formulation be in the form of an intimate mixture. The formulation components are milled together until a suitable mixture has been obtained. It is ordinary to use elevated temperatures to assist in the mixing. It is necessary with these defined polyperoxy compounds to control the mixing temperature—and at higher temperatures, the mixing time—to avoid premature curing or localized curing. In the case of elastomers, the Banbury mixers may reach a working temperature of 250°–260° F.; therefore, it is necessary that the vulcanizible composition have a cure time at these temperatures which permits good mixing without the premature cure, known as scorching in the rubber industry.

The defined polyperoxy compound(s) is present in the vulcanizible composition of the invention in an amount sufficient to afford the desired degree of cross-linking. The amount needed is very much dependent on the type of polymeric compound present and the types and amounts of coagent and promoters present. In general 0.01 equivalents of a peroxide will cure 100 grams of EPR (for a difunctional peroxide the equivalent weight is one half the molecular weight). Different end uses however, will require more or less cross-links, so frequently an excess of 25 to 100% is used.

The vulcanizible compositions of the invention are "stable" at ordinary atmospheric temperatures and may be shipped and stored for normal periods without undergoing undesirable premature partial curing.

VULCANIZED COMPOSITIONS

The vulcanizible composition is heat cured to a time sufficient to obtain the desired degree of cross-linking (vulcanization). The heat curing has a temperature-time relation which is primarily dependent on the polymeric compound and the polyperoxy agent present but is affected by the formulation as a whole. It is customary to use a time equal to about 6–8 half-lives of the polyperoxy agent.

In the case of elastomers, the vulcanizing may be carried out at a temperature of about 270°–600° F., or more. The cure time is inversely related to temperature. It may be from about 1 minute at about 400° F. to about 240 minutes (4 hours) at 270° F. for EPR formulations. The defined polyperoxy agents give acceptable cure times at the lower temperatures which is advantageous to producers as lower temperatures reduce the possibility of "burning" and the shorter times permit a greater output on a given piece of equipment. In the case of EPR formulations, the preferred polyperoxy agents heat cure at a temperature-time relation: about 300°–325° F. and about 8–30 minutes, where the longer times are associated with the lower temperatures. With EPR formulations, however, somewhat longer times may be used without significant degradation of the product.

The heat cured (vulcanized) product may develop better physical properties on maturing at ordinary temperatures. In the case of elastomers such a period seems desirable; a 16–24 hour maturing period is sufficient.

The heat curing may be carried in any of the manners now used by the polymer compounding and rubber compounding art. These might be mold cures; or oil-bath cures, where oil does not harm the polymeric compound; or even cures; or steam cures; or hot metal bath cures.

ILLUSTRATIONS

Embodiments of vulcanizible compositions, vulcanized compositions and a method of heat curing are set out hereinafter.

In these embodiments the polymeric compound was an ethylene-propylene rubber sold by Enjay Chemical Company and having about a 40:60 ethylene:propylene content; no oil extender was present. A carbon black reinforcing material was present. Sulfur was used as a coagent. The standard formulation was: EPR, 100 parts by weight; carbon black, 50 or 60 PHR; sulfur, 0.3 PHR; and the polyperoxy cross-linking agent—no carrier was present, unless so stated.

The ingredients of the embodiment formulation were milled to an intimate plastic mixture on a standard roll mill, such as used in the rubber industry. The temperature of the mix during milling was held below 250° F. At these conditions no scorching occurred in any embodiment.

The intimately mixed vulcanizible mass was removed from the roll mill and a portion placed in a mold and heat cured in a hydraulic press. The standard curing time was about 20–≅minutes at 300° F. Other temperatures and times of course may be used; the higher temperatures requiring shorter cure times.

Immediately upon removal from the curing press, the cured slabs are permitted to mature at room temperature for about 24 hours. This time was sufficient to give reproducible results from control compositions.

The matured slabs were then cut into dumbell shaped specimens and tested for tensile strength on an Instron Tensile Tester, following ASTM procedure as prescribed in D412-61T, "Tension Testing of Vulcanized Rubber".

The target for commercial quality cured EPR composition was a 300% modulus of 1500±100 psi. It was found that to attain this level of cure, about 0.013 equivalents of polyperoxide compound is required.

The odor quality of the vulcanized compositions was determined by a standardized odor panel procedure. The odor of the best known composition was rated "1", while an unacceptable composition was rated "5". The ratings involved both the intensity and the character of the odor.

EXAMPLE 1

At 2.3 PHR (0.013 equivalents active oxygen) the n-butyl gamma, gamma bis(t-butylperoxy) valerate gave satisfactory results on tensile testing and had an odor quality so excellent that a 1 rating was given only because this was the lowest rating on the scale.

EXAMPLE 2

The methyl gamma, gamma bis(t-butylperoxy) valerate gave results approaching Example 1, although somewhat less efficient.

EXAMPLE 3

The biester, ethylene gamma, gamma bis(t-butylperoxy) valerate gave results comparable to Example 2.

EXAMPLE 4

The n-dodecyl gamma, gamma bis(t-butylperoxy) valerate gave a 1 odor rating.

EXAMPLE 5

The allyl gamma, gamma bis(t-butylperoxy) valerate gave results comparable to Example 1 except that the odor rated 2.

EXAMPLE 6

The 2-ethylhexyl gamma, gamma bis(t-butylperoxy) valerate was not only less efficient than the straight chain esters but also gave an odor rating of 3—still good by commercial standards.

EXAMPLE 7

The isopropyl gamma, gamma bis(t-butylperoxy) valerate was somewhat less efficient than Example 1 and gave a high odor rating.

EXAMPLE 8

The ethyl, 2,2-bis(t-butylperoxy) propionate was much less efficient and gave a high odor rating.

EXAMPLE 9

The ethyl, 3,3-bis(t-butylperoxy) butyrate gave good efficiency but a high odor rating.

EXAMPLE 10

The n-butyl, 5,5-bis(t-butylperoxy) hexanoate gave good efficiency and a satisfactory odor.

EXAMPLE 11

The n-butyl, 6,6-bis(t-butylperoxy) heptanoate gave good efficiency but had a high odor rating.

EXAMPLE 12

The diethyl, 4,4-bis(t-butylperoxy) heptane-1,7-dioate gave somewhat poorer performance than did the ester of Example 11.

EXAMPLES 13-16

The metal salts of gamma, gamma bis(t-butylperoxy) valerate were tested as the barium, calcium, lithium and zinc compounds respectively.

EXAMPLE 17

The gamma, gamma bis(t-butylperoxy) levulinic acid itself was about as efficient as the n-butyl ester but gave a higher odor rating.

EXAMPLE 18

The gamma, gamma bis(t-butylperoxy) levulinic acid anhydride was somewhat less efficient than the acid itself but gave a better odor rated product.

EXAMPLE 19

A formulation was tested using a 50:50 silicate carrier: n-butyl gamma, gamma bis(t-butylperoxy) valerate in the same ester content as Example 1. The results were, within reproducibility of the test procedure, the same as for the ester of Example 1.

EXAMPLE 20 n-butyl gamma, gamma bis(t-amylperoxy) levulinate was prepared and tested. In a formulation having 0.03 equivalents of active oxygen, the formulation cured but had a high odor rating.

TESTS 21-28

Eight bis(t-butylperoxy) alkanes having 3-8 carbon atoms in the alkane group were prepared and tested in the standard formulation. All of these were very much less efficient than the prefered polyperoxy compounds; each had oxygen requirements in excess of 200% of theory; and in all instances the odor rating was very high.

OTHER TESTS

Formulations were made with the commonly used peroxide curing agents. These were found to give good efficiencies, and good or satisfactory odors but required curing at 320° F. or higher to give an acceptably short curing time.

EXAMPLES 29-31

Three polyperoxy esters were used as curing agents for a styrene-polyester resin blend; 1% by weight of agent per 100 parts by weight of blend. These esters were n-butyl gamma, gamma bis(t-butylperoxy) valerate (No.29); n-butyl gamma, gamma bis(t-amylperoxy) valerate (No.30); and n-butyl gamma, gamma bis(-pinanylperoxy) valerate (No.31). The blend was prepared by mixing 7 parts by weight of resin and 3 parts by weight of styrene monomer. The resin was the polycondensate of maleic anhydride, 1.0 mole; phtholic anhydride, 1.0 mole; and propylene glycol, 2.2 moles; the polyester resin had an acid No. of 45-50.

The S.P.I. gel times, cure times and exotherms were determined (S.P.I. procedure for running exotherm curves—Polyester Resins; Modern Plastics 39, pp 147 ff, August 1962); also the Barcol hardness I and II. These tests were run at 212° F. The results are set out below.

|  | No. 29 | No. 30 | No. 31 |
| --- | --- | --- | --- |
| Gel, minutes | 10.2 | 7.3 | 7.4 |
| Cure, minutes | 12.3 | 9.0 | 9.0 |
| Peak Exotherm, °F. | 448 | 446 | 442 |
| Barcol I | 40-45 | 45-50 | 45-48 |
| Barcol II | 45-48 | 45-48 | 45-48 |

These results are outstanding for peroxy curing agents.

EXAMPLE 32

Here 2.5 PHR of n-butyl gamma, gamma bis(t-butylperoxy) valerate and 100 PHR of a low density polyethylene (Bakelite) were milled into intimate admixture. The mix was made into slabs and cured at 356° F. for 5 minutes. The slabs and test strips were so described as Example 1. The Instron results were: ultimate tensile, 2460 psi; 300% modulus, 1280 psi; % elongation, 575. The percent cross-linking as determined by the ASTM solvent extraction procedure was 79.4%; the polyethylene charge had zero cross-linking.

While numerous illustrative compounds and embodiments of the invention have been set forth, it is to be understood the invention is not limited thereto and is limited only by the aforesaid description.

Thus having described the invention, what is claimed is:

1. A polyperoxy compound of the formula:

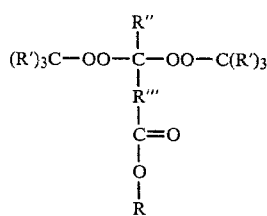

where:

R is an alkyl having 1–18 carbons;

(R')₃C— is an alkyl having 4–24 carbons;

R" is an alkyl or an alkyl substituted by —COOR₅ where R₅ is an alkyl having 1–18 carbons;

R''' is a direct bond or an alkylene diradical; and

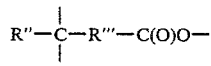

has 3 to 18 carbons.

2. A polyperoxy compound having the formula:

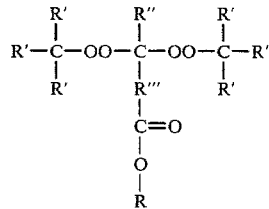

where:

R is an alkyl having 1–18 carbons;
(R')₃—C— is an alkyl having 4–24 carbons;
R" is alkyl;
R''' is alkylene; and

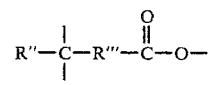

has 4 to 7 carbons.

3. Diethyl 4,4-bis(t-butylperoxy)heptane-1,7-dioate.
4. Ethyl 2,2-bis(t-butylperoxy)propionate.
5. Ethyl 3,3-bis(t-butylperoxy)butyrate.
6. n-Butyl 4,4-di(t-butylperoxy) valerate.

* * * * *

UNITED STATES PATENT AND TRADEMARK OFFICE
CERTIFICATE OF CORRECTION

PATENT NO. : 4,328,360

DATED : May 4, 1982

INVENTOR(S) : Wilbur H. McKellin et al

It is certified that error appears in the above—identified patent and that said Letters Patent is hereby corrected as shown below:

On the title page Inventors should read:

-- Wilbur H. McKellin, Buffalo; Orville L. Mageli, Kenmore, all of N. Y. --.

Signed and Sealed this

Twenth-eighth Day of September 1982

[SEAL]

Attest:

Attesting Officer

GERALD J. MOSSINGHOFF

Commissioner of Patents and Trademarks